US005599966A

United States Patent [19]
Bron et al.

[11] Patent Number: 5,599,966
[45] Date of Patent: Feb. 4, 1997

[54] SUBSTITUTED ETHANOLAMINE ESTERS

[75] Inventors: Jan Bron, Giessenburg; Geert J. Sterk, Utrecht; Hendrik Timmerman, Voorschoten; Meta E. J. Veerman; Jan F. Van Der Werf, both of Amsterdam, all of Netherlands

[73] Assignee: BYK Nederland BV, Zwanenburg, Netherlands

[21] Appl. No.: 416,860

[22] PCT Filed: Oct. 18, 1993

[86] PCT No.: PCT/EP93/02862

§ 371 Date: Apr. 17, 1995

§ 102(e) Date: Apr. 17, 1995

[87] PCT Pub. No.: WO94/08945

PCT Pub. Date: Apr. 28, 1994

[30] Foreign Application Priority Data

Oct. 16, 1992 [CH] Switzerland ............... 03230/92

[51] Int. Cl.$^6$ .......... C07C 255/49; C07C 229/08; C07D 213/55; C07D 209/16
[52] U.S. Cl. .......... 558/414; 546/335; 548/504; 549/77; 549/491; 560/12; 560/39; 560/61; 560/100; 560/105
[58] Field of Search .............. 560/39, 12, 61, 560/100, 105; 546/329, 335; 548/503, 504; 549/378, 77, 491; 558/414

[56] References Cited

U.S. PATENT DOCUMENTS 4,337,207  6/1982  Goodman ................... 554/55

FOREIGN PATENT DOCUMENTS

| 893088 | 4/1962 | European Pat. Off. . |
| 0181709 | 5/1986 | European Pat. Off. . |
| 1126889 | 4/1962 | Germany . |
| 893088 | 4/1962 | United Kingdom . |
| 1178191 | 1/1970 | United Kingdom . |
| 1460593 | 1/1977 | United Kingdom . |

*Primary Examiner*—Joseph Conrad
*Attorney, Agent, or Firm*—Jacobson, Price, Holman & Stern, PLLC

[57] ABSTRACT

Compounds of the formula (I): $Ar_1$—CH(OH)—$CH_2$—NH—$CH_2$—X—$CH_2$—E—$(CH_2)_n$—Y—$Ar_2$, in which the substituents and symbols have the meanings given in the description, are novel active compounds having, in particular, a broncholytic action.

11 Claims, No Drawings

SUBSTITUTED ETHANOLAMINE ESTERS

FIELD OF USE OF THE INVENTION

The invention relates to novel compounds, processes for their preparation and their use as active compounds in medicaments.

KNOWN TECHNICAL BACKGROUND

German Patent Applications DE 37 04 223 and DE 40 28 398 and European Patent Applications EP 278 727, EP 278 728, EP 286 242, EP 303 464, EP 303 465, EP 303 466 and EP 422 889 describe variously substituted ethanolamine derivatives which, because of their $\beta_2$ adrenoceptor-agonistic properties, are said to be particularly suitable for the treatment of diseases of the respiratory passages. British Patent 893,088 describes substituted amines which are said to have antihypertensive and in some cases also spasmolytic properties. The compounds disclosed in this patent are phenylethylamines substituted in a particular manner, which are substituted on the nitrogen atom by an alkyleneoxycarbonylphenyl radical, where this phenyl radical bonded directly to the carbonyl group must be substituted by three hydroxyl or alkoxy groups. German Auslegeschrift 11 26 889 likewise describes substituted amines (derived from reserpine) having an antihypertensive and spasmolytic action, in which the phenyl radical bonded directly to the carbonyl group must be substituted by at least one hydroxyl or alkoxy radical and if appropriate also by a further hydroxyl or alkoxy radical.

DESCRIPTION OF THE INVENTION

A novel group of substituted ethanolamine derivatives which differ structurally from the compounds of the prior art by a hydrolyzable ester group or by a longer chain length or a quite specific substitution has now been found. In a first aspect, the invention thus relates to compounds of formula I

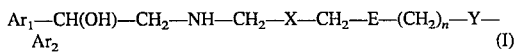

in which

X is 1–12C-alkylene, 1–6C-alkylenoxy-1–6C-alkylene or cyclohexylene,

E is carbonyloxy (—CO—O—) or oxycarbonyl (—O—CO—), n is an integer from 0 to 10, Y is a bond, oxygen (O), sulfur (S), the group —CHR—, in which R is 1–4C-alkyl, phenyl or hydroxyl, or the group —CR'$_2$— or —CHR'—CH$_2$O—, in which R' is 1–4C-alkyl, and in which Y is not oxygen if n is the number 0, Ar$_1$ is a phenyl radical substituted by R1, R2 and R3, in which R1 is hydrogen, halogen, hydroxyl (—OH), amino (—NH$_2$), ureido (—NH—CO—NH$_2$), formylamino (—NH—COH), 1–4C-alkylcarbonylamino (—NH—CO-1–4C-alkyl), di-1–4C-alkyl-carbamoyloxy [—O—CO—N(1–4C-alkyl)$_2$], toluyloxy (—O—CO—C$_6$H$_4$—CH$_3$), hydroxymethyl (—CH$_2$OH), 1–4C-alkylcarbonyloxy (—O—CO-1–4C-alkyl), 1–4C-alkyl, 1–4C-alkoxy, 1–4C-alkylsulfonylamino (—NH—SO$_2$-1–4C-alkyl), 1–4C-alkylsulfonylmethyl (—CH$_2$—SO$_2$-1–4C-alkyl) or 1–4C-alkoxy-1–4C-alkyl, R2 is hydrogen, halogen, hydroxyl (—OH), cyano (—CN), trifluoromethyl (—CF$_3$), toluyloxy (—O—CO—C$_6$H$_4$—CH$_3$), hydroxymethyl (—CH$_2$OH) or 1–4C-alkylcarbonyloxy (—O—CO-1–4C-alkyl) and R3 is hydrogen or halogen, and Ar$_2$ is a phenyl radical which is substituted by R4 and R5, a thienyl radical, a pyridyl radical, a naphthyl radical, an indolyl radical, an indanyl radical or a benzo-1,4-dioxanyl radical, in which R4 is hydrogen, halogen, hydroxyl (—OH), cyano (—CN), 1–4C-alkyl, 1–4C-alkoxy, benzyloxy, nitro (—NO$_2$), trifluoromethyl (—CF$_3$), 1–4C-alkoxycarbonyl (—CO—O-1–4C-alkyl), carbamoyl (—CO—NH$_2$), di-1–4C-alkylcarbamoyl [—CO—N(1–4C-alkyl)$_2$], amino (—NH$_2$), 1–4C-alkylsulfonyl, phenyl or phenylcarbonylamino and R5 is hydrogen, halogen, hydroxyl (—OH), 1–4C-alkyl or 1–4C-alkoxy, and in which R4 is not hydroxyl or 1–4C-alkoxy if E is oxycarbonyl (—O—CO—), n is the number 0 and Y is a bond, and in which R1 and R2 are not simultaneously hydroxyl if X is 1–4C-alkylene and E is carbonyloxy (—CO—O—), and the salts of these compounds.

1–12C-alkylene is straight-chain or branched alkylene radicals having 1 to 12 carbon atoms. Examples which may be mentioned are the radicals methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), pentamethylene (—CH$_2$CH$_2$CH$_2$CH$_2$CH$_2$—), hexamethylene (—CH$_2$—(CH$_2$)$_4$—CH$_2$—), octamethylene (—CH$_2$—(CH$_2$)$_6$—CH$_2$—), decamethylene (—CH$_2$—(CH$_2$)$_8$—CH$_2$—), dodecamethylene (—CH$_2$—(CH$_2$)$_{10}$—CH$_2$—), 1,2-dimethylethylene [—CH(CH$_3$)—CH(CH$_3$)—], 1,1-dimethylethylene [—C(CH$_3$)$_2$—CH$_2$—], isopropylidene [—C(CH$_3$)$_2$—], 2,2-dimethylpropylene [—CH$_2$—C(CH$_3$)$_2$—CH$_2$—], 2-methylpropylene [—CH$_2$—CH(CH$_3$)—CH$_2$—] and 2-methylethylene [—CH$_2$—CH(CH$_3$)—].

1–6C-alkyleneoxy-1–6C-alkylene is straight-chain or branched alkylene radicals having 1 to 6 carbon atoms, which are substituted by straight-chain or branched 1–6C-alkyleneoxy radicals. Examples which may be mentioned are the ethoxyethylene (—CH$_2$—CH$_2$—O—CH$_2$—CH$_2$—) and the methoxymethylene radical (—CH$_2$—O—CH$_2$—).

Cyclohexylene radicals which may be mentioned are the 1,2-, the 1,3- and, in particular, the 1,4-cyclohexylene radical.

1–4C-alkyl is straight-chain or branched alkyl radicals having 1 to 4 carbon atoms. Examples which may be mentioned are the butyl, isobutyl, sec-butyl, tert-butyl, propyl, isopropyl, ethyl and, in particular, the methyl radical.

Halogen in the context of the present invention is bromine, chlorine and fluorine.

A 1–4C-alkylcarbonylamino radical which may be mentioned is, for example, the acetylamido radical (—NH—CO—CH$_3$).

A di-1–4C-alkylcarbamoyloxy radical which may be mentioned is, for example, the dimethylcarbamoyloxy radical [—O—CO—N(CH$_3$)$_2$].

1–4C-alkylcarbonyloxy radicals which may be mentioned are, for example, the tert-butylcarbonyloxy radical and the isopropylcarbonyloxy radical.

1–4C-alkoxy radicals contain, in addition to the oxygen atom, one of the abovementioned 1–4C-alkyl radicals. The methoxy radical is preferred.

A 1–4C-alkylsulfonylamino radical which may be mentioned is, for example, the methylsulfonylamino radical (—NH—SO$_2$—CH$_3$).

A 1–4C-alkylsulfonylmethyl radical which may be mentioned is, for example, the methylsulfonylmethyl radical (—CH$_2$—SO$_2$—CH$_3$).

A 1–4C-alkoxy-1–4C-alkyl radical which may be mentioned is the methoxymethyl radical (—CH$_2$—O—CH$_3$).

Radicals Ar$_1$ which may be mentioned by way of example are the radicals 4-aminophenyl, 3,4-dihydroxyphenyl, 3,5-dihydroxyphenyl, 3,5-bis-dimethylaminocarbonyloxyphenyl, 3,5-bis-tolyloxyphenyl, 4-hydroxy-3-ureidophenyl, 3-formylamino-4-hydroxyphenyl, 4-hydroxyphenyl, 3-amino-5-hydroxyphenyl, 2-fluorophenyl, 3-amino-5-hydroxymethylphenyl, 4-amino-3-cyanophenyl, 3,5-di-tert-butylcarbonyloxyphenyl, 3,5-diisopropylcarbonyloxyphenyl, 2-chloro-4-hydroxyphenyl, 2-fluoro-4-hydroxyphenyl, 3-fluoro-4-hydroxyphenyl, 4-hydroxy-3-methoxyphenyl, 4-hydroxy-3-methoxymethylphenyl, 4-hydroxy-3-methylsulfonamidophenyl and 4-hydroxy-3-methylsulfonylmethylphenyl.

Radicals Ar$_1$ which may be singled out are the radicals phenyl, 2-chlorophenyl, 3-hydroxyphenyl and 4-amino-3-chloro-5-trifluoromethylphenyl.

Preferred radicals Ar$_1$ which may be mentioned are the radicals 3-hydroxymethyl-4-hydroxyphenyl, 4-amino-3,5-dichlorophenyl and 4-amino-3-chloro-5-cyanophenyl.

1–4C-alkoxycarbonyl radicals R4 which may be mentioned are the methoxycarbonyl and the ethoxycarbonyl radical.

A di-1–4C-alkylcarbamoyl radical R4 which may be mentioned is the diethylcarbamoyl radical.

A 1–4C-alkylsulfonyl radical R4 which may be mentioned is the methylsulfonyl radical.

Radicals Ar$_2$ which may be singled out are the radicals phenyl, 3-fluorophenyl, 4-fluorophenyl, 4-methoxyphenyl, 2-trifluoromethylphenyl, 3-trifluoromethylphenyl, 2-nitrophenyl, 3-nitrophenyl, 4-nitrophenyl, 2-methylphenyl, 4-methylphenyl, 4-benzyloxyphenyl, 3,5-dimethylphenyl, 4-propoxyphenyl, 2-cyanophenyl, 4-cyanophenyl, 4-methylsulfonylphenyl, 4-bromophenyl, 2-chloro-6-fluorophenyl, 3-chlorophenyl, 4-chlorophenyl, 4-ethoxyphenyl, 2-phenylcarbonylaminophenyl, 2-phenylphenyl, 3-phenylphenyl, 4-phenylphenyl, 2-naphthyl, 2-thienyl, 3-thienyl, 3-pyridyl, 2-indanyl and 2-benzodioxanyl.

Preferred radicals Ar$_2$ which may be mentioned are the radicals 2-hydroxyphenyl, 3-hydroxyphenyl, 4-hydroxyphenyl, 2-fluorophenyl, 3-methylphenyl, 2-methoxyphenyl, 3-methoxyphenyl, 2-chlorophenyl, 1-naphthyl, 3-indolyl and 2-pyridyl.

Possible salts for compounds of formula I are preferably all the acid addition salts. The pharmacologically tolerated salts of the inorganic and organic acids usually used in pharmaceuticals may be mentioned in particular. Pharmacologically non-tolerated salts which, for example, may initially be obtained as process products during preparation of the compounds according to the invention on an industrial scale are converted into pharmacologically tolerated salts by processes known to the expert. Suitable such salts are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed for the salt preparation in a ratio of amounts which is equimolar or deviates therefrom—depending on whether the acid is mono- or polybasic and depending on what salt is desired.

The compounds of formula I contain at least one chirality center [on the carbon atom —CH(OH)—], and further chirality centers may also additionally be present by appropriate branchings in the groups X and Y. The invention relates to all the enantiomers and diastereomers as well as mixtures thereof, including racemates. Compounds of formula I in which the substituents on the carbon atom —CH(OH)— are arranged in the absolute configuration R (in accordance with rules of Cahn, Ingold and Prelog) are preferred.

Compounds of formula I which are to be singled out are those in which

X is 1–6C-alkylene, 1–2C-alkyleneoxy-1–2C-alkylene or cyclohexylene,

E is carbonyloxy (—CO—O—) or oxycarbonyl (—O—CO—), n is an integer from 1 to 5,

Y is a bond, oxygen (O) or the group —CHR—, in which R is 1–4C-alkyl,

Ar$_1$ is a phenyl radical substituted by R1, R2 and R3, in which

R1 is hydrogen, hydroxyl or amino (—NH$_2$),

R2 is hydrogen, halogen, cyano, trifluoromethyl or hydroxymethyl and

R3 is hydrogen or halogen, and

Ar$_2$ is a phenyl radical substituted by R4 and R5, a thienyl radical, a pyridyl radical, a naphthyl radical, an indolyl radical or an indanyl radical, in which R4 is hydrogen, halogen, hydroxyl (—OH), cyano (—CN), 1–4C-alkyl, 1–4C-alkoxy, benzyloxy, nitro (—NO$_2$) or trifluoromethyl (—CF$_3$), and R5 is hydrogen, halogen or 1–4C-alkyl, and the salts of these compounds.

Compounds of the formula I which are to be singled out in particular are those in which X is 3–4C-alkylene, E is carbonyloxy (—CO—O—) or oxycarbonyl (—O—CO—), n is the number 1 or 2, Y is a bond, Ar$_1$ is phenyl, 4-amino-3-chloro-5-cyanophenyl, 4-hydroxy-3-hydroxymethylphenyl or 4-amino-3,5-dichlorophenyl, and Ar$_2$ is a phenyl radical substituted by R4 and R5 or a 1-naphthyl radical, in which R4 is hydrogen, chlorine, fluorine, hydroxyl (—OH), 1–4C-alkyl or 1–4C-alkoxy and R5 is hydrogen, and the salts of these compounds.

Compounds according to the invention which may be mentioned by way of example are

[6-(2-hydroxy-2-phenylethylamino)-1-hexyl]diphenylacetate,

[6-(2-hydroxy-2-phenylethylamino)-1-hexyl]2-phenylbutanoate,

[7-(2-hydroxy-2-phenylethylamino)-1-heptyl]4-phenylbutanoate, 3-phenylpropyl 4-(2-hydroxy-2-phenylethylamino)butanoate,

[6-(2-hydroxy-2-phenylethylamino)-1-hexyl]nicotinate, 2-(2-hydroxyphenoxy)ethyl 6-[2-(4-amino-3,5-dichlorophenyl)-2-hydroxyethylamino]hexanoate, {6-[2-(4-amino-3,5-dichlorophenyl)-2-hydroxyethylamino]-1-hexyl}phenyl glycolate, 2-(2-trifluoromethylphenyl)ethyl 6-[2-(4-amino-3,5-dichlorophenyl)-2-hydroxyethylamino]hexanoate, 2-phenylethyl 6-[2-(4-amino-3,5-dichlorophenyl)-2-hydroxyethylamino]hexanoate, 3-phenylpropyl 6-[2-(4-amino-3,5-dichlorophenyl)-2-hydroxyethylamino]hexanoate, 5-phenylpentyl 6-[2-(4-amino-3,5-dichlorophenyl)-2-hydroxyethylamino]hexanoate, 2-(4-benzyloxyphenoxy)ethyl 6-[2-(4-amino-3,5-dichlorophenyl)-2-hydroxyethylamino]hexanoate, 2-(3,5-dimethylphenoxy)ethyl 6-[2-(4-amino-3,5-dichlorophenyl)-2-hydroxyethylamino]hexanoate, 3-(4-hydroxyphenyl)propyl 6-[2-(4-amino-3,5-dichlorophenyl)-2-hydroxyethylamino]hexanoate, 2-(4-propoxyphenoxy)ethyl 6-[2-(4-amino-3,5-dichlorophenyl)-2-hydroxyethylamino]hexanoate, 4-phenylbutyl [6-(2-hydroxy-2-phenylethylamino)]hexanoate, 2-(2-nitrophenyl)ethyl 6-[2-(4-amino-3,5-dichlorophenyl)-2-hydroxyethylamino]hexanoate, 2-(2-cyanophenoxy)ethyl 6-[2-(4-amino-3,5-dichlorophenyl)-2-hydroxyethylamino]hexanoate, {6-[2-(4-amino-3,5-dichlorophenyl)-2-hydroxyethylamino]-1-hexyl}5-phenylvalerate and the salts of these compounds.

The invention furthermore relates to a process for the preparation of compounds of the formula I and their salts. The process comprises a) for the preparation of compounds I in which E is oxycarbonyl, reacting compounds of formula II $$Ar_1\text{—CH(OH)—CH}_2\text{—NH}_2 \quad (II)$$

in which $Ar_1$ has the abovementioned meaning, with compounds of formula III $$L\text{—CH}_2\text{—X—CH}_2\text{—O—CO—(CH}_2)_n\text{—Y—Ar}_2 \quad (III)$$

in which X, n, Y and $Ar_2$ have the abovementioned meanings and L is a suitable leaving group, or b) for the preparation of compounds I in which E is carbonyloxy, reacting compounds of formula II $$Ar_1\text{—CH(OH)—CH}_2\text{—NH}_2 \quad (II)$$

in which $Ar_1$ has the abovementioned meaning, with compounds of formula IV $$L\text{—CH}_2\text{—X—CH}_2\text{—CO—O—(CH}_2)_n\text{—Y—Ar}_2 \quad (IV)$$

in which X, n, Y and $Ar_2$ have the abovementioned meanings and L is a suitable leaving group, or c) for the preparation of compounds I in which E is oxycarbonyl, reacting compounds of formula V $$Ar_1\text{—CH(OH)—CH}_2\text{—NH—CH}_2\text{—X—CH}_2\text{—OH} \quad (V)$$

in which $Ar_1$ and X have the abovementioned meanings, with compounds of formula VI $$Z\text{—CO—(CH}_2)_n\text{—Y—Ar}_2 \quad (VI)$$

in which n, Y and $Ar_2$ have the abovementioned meanings and Z is OH (hydroxyl) or a suitable leaving group, and, if desired, subsequently converting compounds I obtained according to a), b) or c) into their salts, or, if desired, subsequently liberating the compounds I from resulting salts of compounds I.

The reaction of compounds II with compounds III and IV is carried out in a manner with which the expert is familiar, in inert, preferably polar solvents, for example in methanol, ethanol, 1- or 2-propanol, dimethylformamide, tetrahydrofuran, acetone, methyl ethyl ketone, methyl isobutyl ketone or dioxane, at temperatures between 10° and 120° C., preferably between 50° and 100° C. if appropriate at the boiling point of the solvent used.

The reaction is carried out in the presence of a base, for example a tertiary organic amine, such as diisopropylethylamine, or an inorganic carbonate, such as potassium carbonate.

The expert is familiar with suitable leaving groups L on the basis of his expert knowledge. Thus, for example, the tosylate or the mesylate group, but in particular halogen atoms, and here above all chlorine or bromine, are possible. If chlorine or bromine compounds III or IV are used, the reaction can advantageously also be carried out in the presence of catalytic amounts of an iodide, such as, for example, potassium iodide.

The reaction of compounds V with compounds VI is carried out in a manner known per se, such as is known to the expert on the basis of his expert knowledge of esterification reactions. The esterification is carried out in inert solvents, such as dioxane or tetrahydrofuran, and, depending on the nature of the group Z, either in the presence of an agent which splits off water or bonds water chemically, such as, for example, dicyclohexylcarbodiimide (if Z=OH), or in the presence of 4-toluenesulfonic acid, or in the presence of an auxiliary base (for example triethylamine), if Z is a leaving group, for example a halogen atom (in particular chlorine). The esterification is preferably carried out starting from the carboxylic acid (Z=OH) in a Dean-Stark apparatus under acid reaction conditions as described by M. Bodanszky and A. Bodanszky in: "The Practice of Peptide Synthesis" (Springer-Verlag, Berlin, 1984, page 37).

Depending on the nature of the starting compounds, which can also be employed in the form of their salts, if appropriate, and depending on the reaction conditions, the compounds according to the invention are initially obtained either as such or in the form of their salts.

The salts furthermore are obtained by dissolving the free compounds in a suitable solvent, for example in a chlorinated hydrocarbon, such as methylene chloride or chloroform, a low molecular weight aliphatic alcohol (ethanol or isopropanol), an ether (diisopropyl ether), a ketone (acetone) or water, which contains the desired acid, or to which the desired acid—if appropriate in the precisely calculated stoichiometric amount—is then added.

The salts are obtained by filtration, reprecipitation, precipitation or by evaporation of the solvent.

Resulting salts can be converted into the free compounds by treatment with alkali, for example with aqueous sodium hydrogen carbonate, and the free compounds can in turn be converted into the salts. The compounds can be purified in this manner, or pharmacologically non-tolerated salts can be converted into pharmacologically tolerated salts.

The starting compounds II, III, IV, V and VI are known, or they can be prepared by known processes in an analogous manner, as is described, by way of example, in the examples. Compounds III, for example, can be prepared by reaction of corresponding ω-L-alcohols with suitable carboxylic acids, and compounds IV can be prepared by reaction of corresponding ω-L-carboxylic acids with suitable alcohols (L=leaving group, in particular chlorine or bromine). The reaction is in each case carried out in a Dean-Stark apparatus under acid catalysis, as described, for example, in: Houben-Weyl, Methoden der organischen Chemie [Methods of organic chemistry] VIII/3, pages 503–546. Compounds V are obtained by reaction of correspondingly substituted styrene oxides with suitable amino alcohols, as described, for example, in: Houben-Weyl, Methoden der organischen Chemie [Methods of organic chemistry] VI/3, pages 366–387.

The following general method descriptions and examples serve to illustrate the invention in more detail. The purity and identity of the compounds described in the examples have been confirmed using the following methods:

$^1$H-nuclear magnetic resonance spectrometry (NMR; Bruker AC 200);

High resolution mass spectrometry (Finnigan MT 90);

Melting point (Mettler FP 5 with microscope) or boiling point determination;

Thin layer chromatography (TLC; E. Merck No. 37333, Kieselgel 60 $F_{254}$)

The invention preferably relates to the compounds of formula I mentioned by name in the examples and the salts of these compounds.

EXAMPLES

Starting compounds

General method description for preparation of compounds III and IV:

A solution of 50 mmol of an alcohol L—$CH_2$—X—$CH_2$—OH for compounds III or of 50 mmol of an alcohol HO—$(CH_2)_n$—Y—$Ar_2$ (for compounds IV) is heated with 50 mmol of a carboxylic acid HO—CO—$(CH_2)_n$—Y—$Ar_2$ (for compounds III) or with 50 mmol of a carboxylic acid L—$CH_2$—X—$CH_2$—CO—OH (for compounds IV) and with 0.5 g of 4-toluenesulfonic acid in toluene in a Dean-Stark apparatus until the reaction has ended (TLC control). The toluene is distilled off and the residue is purified by means of distillation, chromatography and/or crystallization. The identity of the resulting starting compounds is characterized by means of $^1$H-NMR.

The following compounds are prepared in accordance with this method description:

A1. 6-bromo-1-hexylbenzoate
From 6-bromo-1-hexanol and benzoic acid. Yield: 85%.

A2. {4-Bromomethyl[trans]cyclohexylmethyl}(3,3-diphenyl)propionate
From 4-bromomethyl[trans]cyclohexylmethanol and 3,3-diphenylpropionic acid. Yield: 60% (oil).

A3. (6-Bromo-1-hexyl)4-phenylbutanoate
From 6-bromo-1-hexanol and 4-phenylbutyric acid. Working up by means of distillation. Yield: 72%. Boiling point: 158° C. (0.01 mbar)

A4. (4-Phenylbutyl)6-bromohexanoate
From 6-bromocaproic acid and 4-phenyl-1-butanol. Working up by means of distillation. Yield: 80%. Boiling point: 158° C. (0.008 mbar).

A5. (6-Bromo-1-hexyl)3-phenylpropionate
From 6-bromo-1-hexanol and 3-phenylpropionic acid. Yield: 85% (oil).

A6. (12-Bromo-1-dodecyl)4-phenylbutanoate
From 12-bromo-1-dodecanol and 4-phenylbutyric acid. Yield: 85% (oil).

A7. Benzyl 6-bromohexanoate
From benzyl alcohol and 6-bromocaproic acid. Yield: 85% (oil).

A8. (6-Bromo-1-hexyl){3-(4-hydroxyphenyl)}propionate
From 6-bromo-1-hexanol and 3-(4-hydroxyphenyl)propionic acid. Working up by means of distillation. Yield: 70%. Boiling point: 205° C. (0.05 mbar).

A9. {4-(Bromomethyl)[trans]cyclohexylmethyl}4-phenylbutanoate
From 4-(bromomethyl)[trans]cyclohexylmethanol and 4-phenylbutyric acid. Yield: 80%.

A10. {2-(1-Naphthyl)ethyl}6-bromohexanoate
From 2-(1-naphthyl)ethanol and 6-bromocaproic acid. Working up by means of distillation. Yield: 88% (oil). Boiling point 150° C. (0.008 mbar).

A11. (3-Phenylpropyl)4-bromobutanoate
From 4-bromobutyric acid and 3-phenylpropanol. Yield: 95%.

A12. (3-Chlorophenyl)3-phenylpropionate
From 3-chloropropanol and 3-phenylpropionic acid. Working up by means of distillation. Yield: 88% (oil). Boiling point 115° C. (0.05 mbar).

A13. {2-(3-Thienyl)ethyl}6-bromohexanoate
From 2-(3-thienyl)ethanol and 6-bromocaproic acid. Yield: 70% (oil).

A14. (9-Bromo-1-nonyl)4-phenylbutanoate
From 9-bromo-1-nonanol and 4-phenylbutyric acid. Yield: 78% (oil).

A15. (2-Phenoxyethyl)6-bromohexanoate
From 2-phenoxyethanol and 6-bromocaproic acid. Yield: 80% (oil).

A16. (6-Bromo-1-hexyl)3-fluorophenylacetate
From 6-bromo-1-hexanol and 3-fluorophenylacetic acid. Yield: 70% (oil).

A17. (6-Bromo-1-hexyl)4-(4-methoxyphenyl)butanoate
From 6-bromo-1-hexanol and 4-(4-methoxyphenyl)butyric acid. Yield: 70% (oil).

A18. (6-Chloro-1-hexyl)phenylacetate
From phenylacetic acid and 6-chloro-1-hexanol. Yield: 80%.

A19. Benzyl 6-bromohexanoate
From benzyl alcohol and 6-bromocaproic acid. Yield: 70% (oil).

A20. (6-Bromo-1-hexyl)3-phenylbutanoate
From 3-phenylbutyric acid and 6-bromo-1-hexanol. Yield: 80% (oil).

A21. {2-(4-Methlphenoxy)ethyl}6-bromohexanoate
From 6-bromocaproic acid and 2-(4-methylphenoxy)ethanol. Yield: 80% (oil).

A22. (12-Bromo-1-dodecyl)2-nitrophenylacetate
From 12-bromo-1-dodecanol and 2-nitrophenylacetic acid. Yield: 80%.

A23. {2-(2-Pyridyl)ethyl}6-bromohexanoate
From 6-bromocaproic acid and 2-(2-pyridyl)ethanol. Yield: 70% (oil).

General method description for preparation of the compounds V:

A solution of 0.1 mol of a styrene oxide

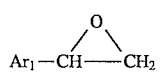

and 0.1 mol of an amino alcohol $NH_2$—$CH_2$—X—$CH_2$—OH in 250 ml of 2-propanol is heated at the boiling point under reflux for 8 hours. The solvent is distilled off and the residue is purified by chromatography.

The following compounds are prepared in accordance with this method description:

B1. 2-(6-Hydroxy-1-hexylamino)1-phenylethanol

From styrene oxide and 6-amino-1-hexanol. Yield after chromatography (methanol): 30% (oil).

B2. 1-(2-Chlorophenyl)2-(6-hydroxy-1-hexylamino)ethanol

From 2-chlorostyrene oxide and 6-amino-1-hexanol. Working up by means of chromatography (ethyl acetate/methanol 1:1). Yield: 41%.

End products

I. General method description for preparation of the end products from starting compounds II and III (process variant a) or from starting compounds II and IV (process variant b):

A solution of 5 mmol of compound II, 4.5 mmol of compound III or IV, 1.0 g of potassium iodide and 3 mmol of diisopropylethylamine in a suitable solvent is heated (if appropriate at the boiling point under reflux) until the reaction has essentially ended (TLC control). The solvent is distilled off and the residue is purified by means of chromatography and/or crystallization. II. General method description for preparation of the end products from the starting compounds V and VI (process variant c):

A mixture of 5 mmol of the compound V, 5 mmol of compound VI (where Z=OH), 7 mmol of 4-toluene-sulfonic acid and 100 ml of toluene is heated in a Dean-Stark apparatus for 5 hours. The toluene is evaporated off, the residue is taken up in ethyl acetate and the mixture is extracted by shaking with an aqueous sodium carbonate solution. The organic phase is dried with magnesium sulfate and evaporated. The residue is purified by means of chromatography and/or crystallization.

The following compounds are prepared analogously to method description I or II:

1. {6-[2-(4-Amino-3,5-dichlorophenyl)-2-hydroxyethylamino]-1-hexyl}benzoate-maleate×½ ethyl acetate According to method I (tetrahydrofuran, reflux 4 days) from 2-amino-1-(4-amino-3,5-dichlorophenyl)ethanol and 6-bromo-1-hexylbenzoate. Working up by means of chromatography (ethyl acetate/petroleum ether 60–80/triethylamine 6:4:1). Recrystallized as the maleate from ethyl acetate. Melting point: 78°–79° C.

2. [6-(2-Hydroxy-2-phenylethylamino)-1-hexyl]benzoate-oxalate

According to method II from 2-(6-hydroxy-1-hexylamino)-1-phenylethanol and benzoic acid. Working up by means of chromatography (ethyl acetate/methanol 1:1). Recrystallized as the oxalate from acetone. Melting point: 121°–125° C.

3. {6-[2-(2-Chlorophenyl)-2-hydroxyethylamino]-1-hexyl}benzoate-oxalate

According to method II from 1-(2-chlorophenyl)-2-(6-hydroxy-1-hexylamino)ethanol and benzoic acid. Working up by means of chromatography (ethyl-acetate/methanol 1:1). Recrystallized as the oxalate from acetone. Melting point: 144°–148° C.

4. {6-[2-(2-Chlorophenyl)-2-hydroxyethylamino]-1-hexyl}-phenyl acetate-oxalate

Preparation according to method II from 1-(2-chlorophenyl)-2-(6-hydroxy-1-hexylamino)ethanol and phenylacetic acid. Working up by means of chromatography (ethyl acetate/methanol/triethylamine 42.5:7.5:1.0). Recrystallized as the oxalate from acetone. Melting point: 114°–117° C.

5. [6-(2-Hydroxy-2-phenylethylamino)-1-hexyl]phenyl acetate-oxalate

According to method II from 2-(6-hydroxy-1-hexylamino)-1-phenylethanol and phenylacetic acid. Working up by means of chromatography (ethyl acetate/methanol 1:1). Recrystallized as the oxalate from acetone. Melting point: 116°–121° C.

6. [6-(2-Hydroxy-2-phenylethylamino)-1-hexyl](3,3-diphenyl)propionate-oxalate

According to method II from 2-(6-hydroxy-1-hexylamino)-1-phenylethanol and 3,3-diphenylpropionic acid. Working up by means of chromatography (ethyl acetate/methanol 1:1). Recrystallized as the oxalate from acetone. Melting point: 136°–139° C.

7. {4-[2-(4-Amino-3,5-dichlorophenyl)-2-hydroxyethylamino-methyl][trans]cyclohexyl methyl}(3,3-diphenylpropionate)maleate According to method I (tetrahydrofuran, reflux 4 days) from 2-amino-1-(4-amino-3,5-dichlorophenyl)ethanol and [4-bromomethyl[trans]cyclohexylmethyl]3,3-diphenylpropionate. Working up by means of chromatography (ethyl acetate/petroleum ether 60–80/triethylamine 4:4:1). Recrystallized as the maleate from ethyl acetate. Melting point: 156°–158° C.

8. {6-[2-(4-Amino-3,5-dichlorophenyl)-2-hydroxyethylamino]-1-hexyl}4-phenylbutanoate-maleate According to method I (tetrahydrofuran, reflux 4 days) from 2-amino-1-(4-amino-3,5-dichlorophenyl)ethanol and (6-bromo-1-hexyl)4-phenylbutanoate. Working up by means of chromatography (ethyl acetate/petroleum ether 60–80/triethylamine 6:4:1). Recrystallized as the maleate from ethyl acetate. Melting point: 69°–74° C.

9. 4-Phenyl-1-butyl 6-[2-(4-amino-3,5-dichlorophenyl)-2-hydroxyethylamino]hexanoate-maleate According to method I (tetrahydrofuran, reflux 4 days) from 2-amino-1-(4-amino-3,5-dichlorophenyl)ethanol and (4-phenylbutyl)6-bromohexanoate. Working up by means of chromatography (ethyl acetate/petroleum ether 60–80/triethylamine 6:4:1). Recrystallized as the maleate from ethyl acetate. Melting point: 77°–79° C.

10. [6-(2-Hydroxy-2-phenylethylamino)-1-hexyl]5-phenylvalerate-oxalate

According to method II from 2-(6-hydroxy-1-hexylamino)-1-phenylethanol and 5-phenylvaleric acid. Working up by means of chromatography (ethyl acetate/methanol 1:1). Recrystallized as the oxalate from acetone. Melting point: 130°–134° C.

11. [6-(2-Hydroxy-2-phenylethylamino)-1-hexyl]4-phenylbutanoate-oxalate

According to method II from 2-(6-hydroxy-1-hexylamino)-1-phenylethanol and 4-phenylbutyric acid. Working up by means of chromatography (ethyl acetate/methanol 1:1). Recrystallized as the oxalate from acetone. Melting point: 124°–129° C.

12. [6-(2-Hydroxy-2-phenylethylamino)-1-hexyl]3-phenylpropionate-oxalate

According to method II from 2-(6-hydroxy-1-hexylamino)-1-phenylethanol and 3-phenylpropionic acid. Working up by means of chromatography (ethyl acetate/methanol 1:1). Recrystallized as the oxalate from acetone. Melting point: 129°–133° C.

13. 4-Phenyl-1-butyl-6-[2-(2-chlorophenyl)-2-hydroxyethylamino]hexanoate-oxalate According to method I (tetrahydrofuran, reflux 4 days) from 2-amino-1-(2-chlorophenyl)ethanol and (4-phenylbutyl)6-bromohexanoate. Working up by means of chromatography (ethyl acetate/petroleum ether 60–80/triethylamine 6:4:1). Recrystallized as the oxalate from acetone. Melting point: 149°–150° C.

14. {6-[2-(4-Amino-3,5-dichlorophenyl)-2-hydroxyethylamino]-1-hexyl}3-phenylpropionate-oxalate According to method I (tetrahydrofuran, reflux 4 days) from 2-amino-1-(4-amino-3,5-dichlorophenyl)ethanol and (6-bromo-1-hexyl)3-phenylpropionate. Working up by means of chromatography (ethyl acetate/petroleum ether 60–80/triethylamine 6:4:1). Recrystallized as the oxalate from acetone. Melting point: 114°–115° C.

15. [12-(2-Hydroxy-2-phenylethylamino)-1-dodecyl]4-phenylbutanoate

According to method I (tetrahydrofuran, reflux 4 days) from 2-amino-1-phenylethanol and (12-bromo-1-dodecyl)4-phenylbutanoate. Working up by means of chromatography (ethyl acetate/petroleum ether 60–80/triethylamine 6:4:1). Recrystallized from diethyl ether. Melting point: 73°–74° C.

16. Benzyl[6-(2-hydroxy-2-phenylethylamino)]hexanoate

According to method I (tetrahydrofuran, reflux 4 days) from benzyl 6-bromohexanoate and 2-amino-1-phenylethanol. Working up by means of chromatography (ethyl acetate/methanol/triethylamine 3:1:0.1). Melting point: 77°–78° C.

17. {6-[2-(4-Amino-3,5-dichlorophenyl)-2-hydroxyethylamino]-1-hexyl}[3-(4-hydroxyphenyl)]propionate-hydrochloride According to method I (dimethylformamide, 2 hours at 90° C.) from 2-amino-1-(4-amino-3,5-dichlorophenyl)ethanol and 6-bromo-1-hexyl{3-(4-hydroxyphenyl)}propionate. The residue after evaporation of the solvent is partitioned in ethyl acetate and 0.2M hydrochloric acid. The organic phase is dried with magnesium sulfate and concentrated. Melting point: 109°–112° C.

18. {4-[2-(4-Amino-3,5-dichlorophenyl)-2-hydroxyethylamino-methyl][trans]cyclohexylmethyl}4-phenylbutanoate-maleate According to method I (dimethylformamide, 2 hours at 90° C.) from 2-amino-1-(4-amino-3,5-dichlorophenyl)ethanol and {4-(bromomethyl)[trans]cyclohexylmethyl}(4-phenyl)butanoate. Working up by means of chromatography (ethyl acetate/petroleum ether 60–80/triethylamine 4:2:1). Recrystallized as the maleate from ethyl acetate. Melting point: 155°–157° C.

19. 2-(1-Naphthyl)ethyl 6-[2-(4-amino-3,5-dichlorophenyl)-2-hydroxyethylamino]hexanoate According to method I (dimethylformamide, 2 hours at 90° C.) from 2-amino-1-(4-amino-3,5-dichlorophenyl)ethanol and {2-(1-naphthyl)ethyl}6-bromohexanoate. Working up by means of chromatography (ethyl acetate/methanol/triethylamine 16:2:1). Recrystallized as the free base from ethyl acetate. Melting point: 60°–61° C.

20. 3-Phenylpropyl-4-[2-(4-amino-3,5-dichlorophenyl)-2-hydroxyethylamino]butanoate-maleate According to method I (dimethylformamide, 2 hours at 90° C.) from 2-amino-1-(4-amino-3,5-dichlorophenyl)ethanol and (3-phenylpropyl)-4-bromobutanoate. Working up by means of chromatography (ethyl acetate/methanol/triethylamine 20:2:1). Recrystallized as the maleate from acetone. Melting point: 70°–71° C.

21. {3-[2-(4-Amino-3,5-dichlorophenyl)-2-hydroxyethylamino]-1-propyl}3-phenylpropionate-oxalate According to method I (tetrahydrofuran, reflux 4 days) from 2-amino-1-(4-amino-3,5-dichlorophenyl)ethanol and (3-chloropropyl)-3-phenylpropionate. Working up by means of chromatography (ethyl acetate/triethylamine 8:1). Recrystallized as the oxalate from acetone. Melting point: 133°–134° C.

22. 2-(3-Thienyl)ethyl6-[2-(4-amino-3,5-dichlorophenyl)-2-hydroxyethylamino]hexanoate According to method I (tetrahydrofuran, reflux 4 days) from {2-(3-thienyl)ethyl}6-bromohexanoate and 2-amino-1-(4-amino-3,5-dichlorophenyl)ethanol. Working up by means of chromatography (ethyl acetate/triethylamine 8:1). Recrystallized as the base from diethyl ether. Melting point: 71°–73° C.

23. 9-(2-Hydroxy-2-phenylethylamino)-1-nonyl4-phenylbutanoate-oxalate

According to method I (tetrahydrofuran, reflux 4 days) from (9-bromo-1-nonyl)4-phenylbutanoate and 2-amino-1-phenylethanol. Working up by means of chromatography (ethyl acetate). Recrystallized as the oxalate from acetone. Melting point: 132°–135° C.

24. 2-Phenoxyethyl6-[2-(4-amino-3,5-dichlorophenyl)-2-hydroxyethylamino]hexanoate According to method I (dimethylformamide, 1 hour at 100° C.) from (2-phenoxyethyl)6-bromohexanoate and 2-amino-1-(4-amino-3,5-dichlorophenyl)ethanol. Working up by means of chromatography (ethyl acetate/methanol/triethylamine 16:2:1). Recrystallized as the base from diethyl ether. Melting point: 46°–47° C.

25. {6-[2-(4-Amino-3,5-dichlorophenyl)-2-hydroxyethylamino]-1-hexyl}3-fluorophenylacetate-oxalate According to method I (dimethylformamide, 3 hours at 90° C.) from (6-bromo-1-hexyl) 3-fluorophenylacetate and 2-amino-1-(4-amino-3,5-dichlorophenyl)ethanol. Working up by means of chromatography (ethyl acetate/methanol/triethylamine 16:2:1). Recrystallized as the oxalate from acetone. Melting point: 70°–71° C.

26. {6-[2-(4-Amino-3,5-dichlorophenyl)-2-hydroxyethylamino]-1-hexyl}4-(4-methoxyphenyl)butanoate-maleate According to method I (dimethylformamide, 2 hours at 90° C.) from (6-bromo-1-hexyl)4-(4-methoxyphenyl)butanoate and 2-amino-1-(4-amino-3,5-dichlorophenyl)ethanol. Working up by means of chromatography (ethyl acetate/triethylamine 5:1). Recrystallized as the maleate from diethyl ether. Melting point: 66°–67° C.

27. {6-[2-(4-Amino-3.5-dichlorophenyl)-2-hydroxyethylamino]-1-hexyl}phenylacetate-hemifumarate According to method I (dimethylformamide, 3 hours at 90° C.) from (6-chloro-1-hexyl)phenylacetate and 2-amino-1-(4-amino-3,5-dichlorophenyl)ethanol. Working up by means of chromatography (ethyl acetate/methanol/triethylamine 8:1:0.5). Recrystallized as the hemifumarate from acetone. Melting point: 79°–82° C.

28. Benzyl6-[2-(4-amino-3,5-dichlorophenyl.)-2-hydroxyethylamino]hexanoate-maleate According to method I (dimethylformamide, 3 hours at 90° C.) from benzyl 6-bromohexanoate and 2-amino-1-(4-amino-3,5-dichlorophenyl)ethanol. Working up by means of chromatography (ethyl acetate/methanol/triethylamine 16:2:1). Recrystallized as the maleate from diethyl ether. Melting point: 54°–55° C.

29. {6-[2-(4-Amino-3,5-dichlorophenyl)-2-hydroxyethylamino]-1-hexyl}3-phenylbutanoate-maleate According to method I (dimethylformamide, 3 hours at 90° C.) from (6-bromo-1-hexyl)3-phenylbutanoate and 2-amino-1-(4-amino-3,5-dichlorophenyl)ethanol. Working up by means of chromatography (ethyl acetate/methanol/triethylamine 20:2:1). Recrystallized as the maleate from ethyl acetate. Melting point: 51°–59° C.

30. 2-(4-Methylphenoxy)ethyl6-[2-(4-amino-3,5-dichlorophenyl)-2-hydroxyethylamino]hexanoate-maleate×½ ethyl acetate According to method I (dimethylformamide, 3 hours at 90° C.) from {2-(4-methylphenoxy)ethyl}6-bromohexanoate and 2-amino-1-(4-amino-3,5-dichlorophenyl)ethanol. Working up by means of chromatography (ethyl acetate/methanol/triethylamine 20:2:1). Recrystallized as the maleate from ethyl acetate. Melting point: 77°–78° C.

31. {12-[2-(4-Amino-3,5-dichlorophenyl)-2-hydroxyethylamino]-1-dodecyl}2-nitrophenylacetate-oxalate According to method I (dimethylformamide, 3 hours at 90° C.) from (12-bromo-1-dodecyl)2-nitrophenylacetate and 2-amino-1-(4-amino-3,5-dichlorophenyl)ethanol. Working up by means of chromatography (ethyl acetate/methanol/triethylamine 20:2:1). Recrystallized as the oxalate from acetone. Melting point: 67°–68° C.

32. 2-(2-Pyridyl)ethyl 6-[2-(4-amino-3,5-dichlorophenyl)-2-hydroxyethylamino]hexanoate-hemifumarate According to method I (dimethylformamide, 1 hour at 90° C.) from {2-(2-pyridyl)ethyl}6-bromohexanoate and 2-amino-1-(4-amino-3,5-dichlorophenyl)ethanol. Working up by means of chromatography (ethyl acetate/methanol/triethylamine 20:2:1). Recrystallized as the hemifumarate from acetone. Melting point: 75°–76° C.

The following compounds are prepared according to method I (in dimethylformamide, 3 hours at 100° C.) from corresponding starting compounds:

33. {6-[2-(4-Amino-3,5-dichlorophenyl)-2-hydroxyethylamino]-1-hexyl}phenoxyacetate, melting point 83°–85° C.
34. {6-[2-(4-Amino-3,5-dichlorophenyl)-2-hydroxyethylamino]-1-hexyl}1-naphthylacetate-maleate, melting point 81°–82° C.
35. {6-[2-(4-Amino-3,5-dichlorophenyl)-2-hydroxyethylamino]-1-hexyl}2-naphthylacetate-hemifumarate, melting point 129°–132° C.
36. 2-(1-Naphthyloxy)ethyl 6-[2-(4-amino-3,5-dichlorophenyl)-2-hydroxyethylamino]hexanoate, melting point 149°–154° C.
37. 2-(4-Hydroxyphenyl)ethyl 6-[2-(4-amino-3,5-dichlorophenyl)-2-hydroxyethylamino]hexanoate, melting point 92°–93° C.
38. {6-[2-(4-Amino-3,5-dichlorophenyl)-2-hydroxyethylamino]-1-hexyl}4-methylsulfonyl-3-nitrophenylacetate-hemifumarate, melting point 111°–113° C.
39. {6-[2-(4-Amino-3,5-dichlorophenyl)-2-hydroxyethylamino]-1-hexyl}3-phenoxypropanoate-hemifumarate, melting point 110°–114° C.
40. {4-[2-(4-Amino-3,5-dichlorophenyl)-2-hydroxyethylamino]-1-butyl}phenylacetate-hemifumarate, melting point 120°–121° C.
41. {5-[2-(4-Amino-2,3-dichlorophenyl)-2-hydroxyethylamino]-1-pentyl}phenylacetate-hemifumarate, melting point 142°–144° C.
42. {7-[2-(4-Amino-3,5-dichlorophenyl)-2-hydroxyethylamino]-1-heptyl}phenylacetate-hemifumarate, melting point 121°–122° C.
43. {8-[2-(4-Amino-3,5-dichlorophenyl)-2-hydroxyethylamino]-1-octyl}phenylacetate-hemifumarate, melting point 116°–118° C.
44. 2-Phenylethyl 7-[2-(4-amino-3,5-dichlorophenyl)-2-hydroxyethylamino]heptanoate-hemifumarate, melting point 127°–129° C.
45. 2-Phenylethyl 8-[2-(4-amino-3,5-dichlorophenyl)-2-hydroxyethylamino]octanoate-hemifumarate, melting point 124°–125° C.
46. 2-Phenylethyl 5-[2-(4-amino-3,5-dichlorophenyl)-2-hydroxyethylamino]pentanoate-fumarate, melting point 139°–143° C.
47. {6-[2-(4-Amino-3,5-dichlorophenyl)-2-hydroxyethylamino]-1-hexyl}4-bromophenylacetate-hemifumarate, melting point 129°–130° C.
48. 2,2-Diphenylethyl 6-[2-(4-amino-3,5-dichlorophenyl)-2-hydroxyethylamino]hexanoate-hemifumarate, melting point 121°–123° C.
49. {6-[2-(4-Amino-3,5-dichlorophenyl)-2-hydroxyethylamino]-1-hexyl}4-phenoxybutanoate-hemifumarate, melting point 112°–113° C.
50. 3-Phenoxy-1-propyl 6-[2-(4-amino-3,5-dichlorophenyl)-2-hydroxyethylamino]hexanoate-hemifumarate, melting point 105°–107° C.
51. {6-[2-(4-Amino-3,5-dichlorophenyl)-2-hydroxyethylamino]-1-hexyl}2-naphthyloxyacetate-hemifumarate, melting point 113°–116° C.
52. {6-[2-(4-Amino-3,5-dichlorophenyl)-2-hydroxyethylamino]-1-hexyl}2-chloro-6-fluorophenylacetate, melting point 130°–132° C.
53. {8-[2-(4-Amino-3,5-dichlorophenyl)-2-hydroxyethylamino]-1-octyl}2-phenoxyacetate-hemifumarate, melting point 124°–125° C.
54. 3-Phenyl-1-propyl 5-[2-(4-amino-3,5-dichlorophenyl)-2-hydroxyethylamino]pentanoate-hemifumarate, melting point 107°–111° C.
55. 2-(3-Hydroxyphenyl)ethyl 6-[2-(4-amino-3,5-dichlorophenyl)-2-hydroxyethylamino]hexanoate-hemifumarate, melting point 157°–159° C.
56. 2-(2-Hydroxyphenyl)ethyl 6-[2-(4-amino-3,5-dichlorophenyl)-2-hydroxyethylamino]hexanoate-hemifumarate, melting point 97°–98° C.
57. 4-Phenyl-1-butyl 5-[2-(4-amino-3,5-dichlorophenyl)-2-hydroxyethylamino]pentanoate-hemifumarate, melting point 130°–132° C.
58. 2-Phenylethyl 6-[2-hydroxy-2-(4-hydroxy-3-hydroxymethylphenyl)ethylamino]hexanoate-oxalate, melting point 119°–122° C.
59. {6-[2-Hydroxy-2-(4-hydroxy-3-hydroxymethylphenyl)ethylamino]-1-hexyl}1-naphthylacetate-xinafoate, melting point 125°–128° C.
60. {6-[2-(4-Amino-3,5-dichlorophenyl)-2-hydroxyethylamino]-1-hexyl}2-thienylacetate-hemifumarate, melting point 127°–129° C.
61. {6-[2-(4-Amino-3,5-dichlorophenyl)-2-hydroxyethylamino]-1-hexyl}2-(4-chlorophenyl)-2-methylpropanoate-hemifumarate, melting point 138°–139° C.
62. {6-[2-(4-Amino-3,5-dichlorophenyl)-2-hydroxyethylamino]-1-hexyl}1-naphthyloxyacetate-hemifumarate, melting point 113°–116° C.
63. 2-(3-Hydroxyphenyl)ethyl 6-[2-hydroxy-2-(4-hydroxy-3-hydroxymethylphenyl)ethylamino]hexanoate-xinafoate, melting point 67°–69° C.
64. 4-Phenylbutyl 6-[2-hydroxy-2-(4-hydroxy-3-hydroxymethylphenyl)ethylamino]hexanoate-oxalate, melting point 119°–121° C.
65. 2-(4-Methylphenyl)ethyl 6-[2-(4-amino-2,3-dichlorophenyl)-2-hydroxyethylamino]hexanoate-hemifumarate, melting point 129°–132° C.
66. 2-(4-Fluorophenyl)ethyl 6-[2-(4-amino-2,3-dichlorophenyl)-2-hydroxyethylamino]hexanoate-hemifumarate, melting point 138°–141° C.
67. {7-[2-(4-Amino-2,3-dichlorophenyl)-2-hydroxyethylamino]-1-heptyl}benzoate-hemifumarate, melting point 142°–144° C.
68. {5-[2-(4-Amino-2,3-dichlorophenyl)-2-hydroxyethylamino]-1-pentyl}3-phenylpropionate-hemifumarate, melting point 129°–130° C.
69. {6-[2-(4-Amino-3,5-dichlorophenyl)-2-hydroxyethylamino]-1-hexyl}4-nitrophenoxyacetate-hemifumarate, melting point 167°–168° C.
70. {6-[2-(4-Amino-3,5-dichlorophenyl)-2-hydroxyethylamino]-1-hexyl}3-methoxyphenylacetate-hemifumarate, melting point 117°–120° C.
71. 2-Phenylethyl 6-[2-(4-amino-3-chloro-5-trifluoromethylphenyl)-2-hydroxyethylamino]hexanoate-hemifumarate, melting point 125°–127° C.
72. {6-[2-(4-Amino-3-chloro-5-trifluoromethylphenyl)-2-hydroxyethylamino]-1-hexyl}1-naphthylacetate-hemifumarate, melting point 141°–144° C.
73. 2-(1-Naphthyl)ethyl 6-[2-(4-hydroxy-3-hydroxymethylphenyl)-2-hydroxyethylamino]hexanoate-xinafoate, melting point 151°–153° C.
74. 2-Phenylethyl 6-[2-(4-amino-5-chloro-3-cyanophenyl)-2-hydroxyethylamino]hexanoate-hemifumarate, melting point 147°–149° C.

75. {6-[2-Hydroxy-2-(4-hydroxy-3-hydroxymethylphenyl)ethylamino]-1-hexyl}phenylacetate-oxalate, melting point 115°–118° C.
76. {5-[2-Hydroxy-2-(4-hydroxy-3-hydroxymethylphenyl)ethylamino]-1-pentyl}(3-hydroxyphenyl)acetatexinafoate, melting point 95°–100° C.
77. {6-[2-(4-Amino-3,5-dichlorophenyl)-2-hydroxyethylamino]-1-hexyl}4-methoxyphenylacetate-hemifumarate, melting point 119°–120° C.
78. {6-[2-(4-Amino-3,5-dichlorophenyl)-2-hydroxyethylamino]-1-hexyl}2-methoxyphenylacetate-hemifumarate, melting point 123°–124° C.
79 {6-[2-(4-Amino-3,5-dichlorophenyl)-2-hydroxyethylamino]-1-hexyl}2-methylphenylacetate, melting point 96°–97° C.
80. {6-[2-(4-Amino-3,5-dichlorophenyl)-2-hydroxyethylamino]-1-hexyl}3-methylphenylacetate-hemifumarate, melting point 130°–132° C.
81. {6-[2-(4-Amino-3,5-dichlorophenyl)-2-hydroxyethylamino]-1-hexyl}2-nitrophenylacetate-hemifumarate, melting point 153°–167° C.
82. {6-[2-(4-Amino-2,3-dichlorophenyl)-2-hydroxyethylamino]-1-hexyl}2-chlorophenylacetate-hemifumarate, melting point 138°–141° C.
83. {6-[2-(4-Amino-2,5-dichlorophenyl)-2-hydroxyethylamino]-1-hexyl}3-chlorophenylacetate-hemifumarate, melting point 119°–122° C.
84. {6-[2-(4-Amino-2,5-dichlorophenyl)-2-hydroxyethylamino]-1-hexyl}4-chlorophenylacetate-hemifumarate, melting point 120°–123° C.
85. 1-(2-Phenyl)propyl 6-[2-(4-amino-3,5-dichlorophenyl)-2-hydroxyethylamino]hexanoate-hemifumarate, melting point 119°–120° C.
86. {5-[2-(4-Amino-3,5-dichlorophenyl)-2-hydroxyethylamino]-1-pentyl}3-(1-naphthyl)propionate-hemifumarate, melting point 127°–128° C.
87. {5-[2-Hydroxy-2-(4-hydroxy-3-hydroxymethylphenyl)ethylamino]-1-pentyl}3-(1-naphthyl)propionate-xinafoate, melting point 114°–115° C.
88. {4-[2-(4-Amino-3,5-dichlorophenyl)-2-hydroxyethylamino]-1-butyl}4-phenylbutyrate-hemifumarate, melting point 126°–127° C.
89. {6-[2-(4-Amino-3,5-dichlorophenyl)-2-hydroxyethylamino]-1-hexyl}4-cyanophenoxyacetate-hemifumarate, melting point 149°–152° C.
90. {6-[2-(4-Amino-3,5-dichlorophenyl)-2-hydroxyethylamino]-1-hexyl}2-fluorophenylacetate-hemifumarate, melting point 136°–137° C.
91. {6-[2-(4-Amino-3,5-dichlorophenyl)-2-hydroxyethylamino]-1-hexyl}4-ethoxyphenylacetate-hemifumarate, melting point 114°–116° C.
92. {6-[2-(4-Amino-5-chloro-3-cyanophenyl)-2-hydroxyethylamino]-1-hexyl}phenylacetate-hemifumarate, melting point 153° C.
93. 3-(1-Naphthyl)propyl 6-[2-(4-amino-3,5-dichlorophenyl)-2-hydroxyethylamino]hexanoate-hemifumarate, melting point 153°–155° C.
94. 3-(1-Naphthyl)propyl 6-[2-(4-hydroxy-3-hydroxymethylphenyl)-2-hydroxyethylamino]hexanoate-xinafoate, melting point 118°–119° C.
95. {6-[2-(4-Amino-5-chloro-3-cyanophenyl)-2-hydroxyethylamino]-1-hexyl}1-naphthylacetate-hemifumarate, melting point 138°–279° C.
96. {6-[2-Hydroxy-2-(3-hydroxyphenyl)ethylamino]-1-hexyl}1-naphthylacetate-hemifumarate, melting point 117°–131° C.
97. {6-[2-(4-Amino-3,5-dichlorophenyl)-2-hydroxyethylamino]-1-hexyl}11-phenoxyundecanoate, melting point 71°–72° C.
98. 1-Phenoxy-2-propyl 6-[2-(4-amino-3,5-dichlorophenyl)-2-hydroxyethylamino]hexanoate-hemifumarate, melting point 103°–105° C.
99. {6-[2-(4-Amino-3,5-dichlorophenyl)-2-hydroxyethylamino]-1-hexyl}2-phenylphenoxyacetate-hemifumarate, melting point 116°–118° C.
100. {6-[2-(4-Amino-3,5-dichlorophenyl)-2-hydroxyethylamino]-1-hexyl}3-phenylphenoxyacetate-hemifumarate, melting point<40° C.
101. {6-[2-(4-Amino-3,5-dichlorophenyl)-2-hydroxyethylamino]-1-hexyl}4-phenylphenoxyacetate-hemifumarate, melting point<40° C.
102. {6-[2-(4-Amino-3,5-dichlorophenyl)-2-hydroxyethylamino]-1-hexyl}2-phenytaminocarbonylphenoxyacetate, melting point 105°–107° C.
103. 2-(3-Indolyl)ethyl 6-[2-(4-amino-3,5-dichlorophenyl)-2-hydroxyethylamino]hexanoate-hemifumarate, melting point 125°–126° C.
104. {6-[2-(4-Amino-3,5-dichlorophenyl)-2-hydroxyethylamino]-1-hexyl}phenylthioacetate-hemifumarate, melting point 154°–155° C.
105. 2-(1,4-Benzodioxanyl)methyl 6-[2-(4-amino-3,5-dichlorophenyl)-2-hydroxyethylamino]hexanoatehemifumarate, melting point 105°–107° C.
106. {2-[2-[2-(4-Amino-3,5-dichlorophenyl)-2-hydroxyethylamino]ethoxy]ethyl}phenylacetate-fumarate, melting point 118°–120° C.
107. 2-Phenylethyl 3-[2-(4-amino-3,5-dichlorophenyl)-2-hydroxyethylamino]propionate-hemifumarate, melting point 128°–131° C.
108. 2-Indanyl 6-[2-(4-amino-3,5-dichlorophenyl)-2-hydroxyethylamino]hexanoate-fumarate, melting point 123°–129° C.

Commercial usefulness

The compounds according to the invention have valuable pharmacological properties which render them commercially usable. They are primarily active β-adrenoceptor agonists (β-sympathomimetics) having preferentially a $β_2$-stimulating action, and they are distinguished in particular by their long duration of action, their stability and selectivity, and by the absence of undesirable side effects.

On the basis of their β-sympathomimetic action, the compounds according to the invention are suitable, for example, for treatment of bradycardias and conduction disturbances and increase the contractility of the heart, they can be employed as tocolytics for treatment of premature labor, they act generally as vasodilators and can be employed for treatment of (peripheral) circulatory disturbances, they lead to a relaxation of the bladder wall musculature and are suitable for treatment of disturbed micturition, they lower the (pathologically increased) internal pressure of the eye and can be employed for treatment of glaucoma, they influence metabolism and are suitable, for example, for treatment of obesity, and on the basis of their above all $β_2$-sympathomimetic action, they are suitable in particular for treatment of diseases of the respiratory passages of varying origin.

In particular, bronchial diseases (induced by allergens or inflammation) can be treated on the basis of the broncholytic activity of the compounds according to the invention. The compounds according to the invention are distinguished here by a low toxicity, a wide therapeutic range, a long-lasting action and reduced systemic side effects. In this connection, the greatly pronounced activity following topical application—compared with systemic administration—is of particular importance.

The broncholytic activity of the compounds according to the invention enables them to be used in human and veterinary medicine, where they are used for treatment and prophylaxis of illnesses based on diseases of the bronchi. For example, acute and chronically obstructive diseases of the respiratory passages of varying origin (bronchitis, allergic bronchitis, bronchial asthma) can be treated in humans and animals. The properties of the compounds according to the invention furthermore enable them to be used for topical treatment of dermatoses, for example for inflammatory and allergic skin diseases, such as toxic and allergic contact eczema, atopical eczema, seborrheic eczema, follicular and superficial pyodermas, endogenous and exogenous acne and acne rosacea.

The compounds according to the invention furthermore are suitable for treatment of those disease states which are known to be influenced positively by administration of certain β-adrenoceptor agonists. Thus, for example, on the basis of the hypoglycemic action of the compounds, metabolic disturbances of varying origin (for example obesity or disturbances such as are related, for example, to diabetes) can be treated. Gastrointestinal motility disturbances and pathological changes in the gastrointestinal tract (for example inflammatory intestinal diseases, such as Colitis ulcerosa or Crohn's disease) can also be treated by the compounds according to the invention.

The invention therefore also relates to a method for treatment of mammals, including humans, suffering from one of the abovementioned diseases. The method comprises administering a therapeutically active and pharmacologically tolerated amount of one or more of the compounds according to the invention to the sick mammal.

The invention also relates to the compounds according to the invention for use for treatment and/or prophylaxis of the diseases mentioned.

The invention furthermore relates to the use of the compounds according to the invention for the preparation of medicaments which are employed for treatment and/or prophylaxis of the diseases mentioned.

The invention furthermore relates to medicaments for treatment and/or prophylaxis of the diseases mentioned which comprise one or more of the compounds according to the invention and/or their pharmacologically tolerated salts.

The medicaments according to the invention are prepared by processes known per se, reference being made to, for example, the statements in European Patent 163 965 in respect of the formulations, the dosage forms (especially in respect of administration by inhalation) and the like. In this connection, administration by inhalation, for which the compounds according to the invention seem outstandingly suitable on the basis of their action profile, is of particular importance in the treatment of bronchial diseases.

If the compounds according to the invention are to be administered by inhalation, daily doses of 0.01 to 2.0 mg, in particular 0.05 to 1.0 mg, advantageously in several individual doses of, for example, 10 to 50 μg of active compound, are administered. For oral administration, correspondingly higher dosages (from 0.5 to 50 mg per day), if appropriate in the form of several individual doses, are to be administered.

Pharmacology

The excellent bronchospasmolytic action of the compounds according to the invention can be demonstrated by in vitro studies on the guinea pig trachea. For this, the relaxing action on a guinea pig trachea which has been contracted beforehand with a suitable dose of methacholine is measured for the compounds to be investigated. The trachea of male guinea pigs (200–300 g) is removed and divided into individual segments and each segment is suspended in an organ bath with 118.5 mM NaCl, 4.7 mM KCl, 1.2 mM $MgSO_4$, 2.5 mM $CaCl_2$, 1.2 mM $KH_2PO_4$, 25 mM $NaHCO_3$ and 10 mM glucose at 37° C. Oxygen to which 5% of $CO_2$ has been added is passed permanently through the solution. After stabilization, the trachea is contracted with a suitable dose of methacholine. Thereafter, a dose/effect curve is plotted with the test substances in a cumulative manner. The concentration (mol/l) which corresponds to 50% of the maximum effect ($EC_{50}$) is then determined from this curve. This $EC_{50}$ is thus a measure of the activity of the compounds according to the invention.

The $-\log[EC_{50}(mol/l)]$ value for selected compounds according to the invention are shown in the following table. The serial number in the table agrees with the number of the compounds in the examples. The number n indicates the number of investigations.

TABLE

| Serial No. | $-\log[EC_{50}]$ | n |
|---|---|---|
| 17 | 7.7 | 6 |
| 19 | 8.2 | 3 |
| 32 | 7.8 | 3 |
| 34 | 8.5 | 5 |
| 37 | 8.7 | 6 |
| 64 | 8.0 | 4 |
| 74 | 8.4 | 6 |
| 82 | 8.0 | 6 |
| 103 | 8.5 | 5 |
| 106 | 8.1 | 3 |

We claim:
1. A compound of formula I

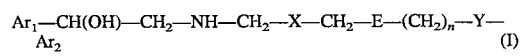

$$Ar_1—CH(OH)—CH_2—NH—CH_2—X—CH_2—E—(CH_2)_n—Y—Ar_2 \quad (I)$$

in which
X is 1–12C-alkylene, 1–6C-alkyleneoxy-1–6C-alkylene or cyclohexylene,
E is carbonyloxy (—CO—O—) or oxycarbonyl (—O—CO—),
n is an integer from 0 to 10,
Y is a bond, oxygen (O), sulfur (S), the group —CHR—, in which R is 1–4C-alkyl, phenyl or hydroxyl, or the group —CR'$_2$— or —CHR'—CH$_2$O—, in which R' is 1–4C-alkyl, and in which Y is not oxygen if n is the number 0,
Ar$_1$ is a phenyl radical substituted by R1, R2 and R3, in which
R1 is hydrogen, halogen, hydroxyl (—OH), amino (—NH$_2$), ureido (—NH—CO—NH$_2$), formylamino (—NH—COH), 1–4C-alkylcarbonylamino (—NH—CO-1–4C-alkyl), di-1–4C-alkyl-carbamoyloxy [—O—CO—N(1–4C-alkyl)$_2$], toluyloxy (—O—CO—C$_6$H$_4$—CH$_3$), hydroxymethyl (—CH$_2$OH), 1–4C-alkylcarbonyloxy (—O—CO-1–4C-alkyl), 1–4C-alkyl, 1–4C-alkoxy, 1–4C-alkylsulfonylamino (—NH—SO$_2$-1–4C-alkyl), 1–4C-alkylsulfonylmethyl (—CH$_2$—SO$_2$-1–4C-alkyl) or 1–4C-alkoxy-1–4C-alkyl,
R2 is hydrogen, halogen, hydroxyl (—OH), cyano (—CN), trifluoromethyl (—CF$_3$), toluyloxy (—O—CO—C$_6$H$_4$—CH$_3$), hydroxymethyl (—CH$_2$OH) or 1–4C-alkylcarbonyloxy (—O—CO-1–4C-alkyl) and

19

R3 is hydrogen or halogen, and

Ar₂ is a phenyl radical which is substituted by R4 and R5, a thienyl radical, a pyridyl radical, a naphthyl radical, an indolyl radical, an indanyl radical or a benzo-1,4-dioxanyl radical, in which R4 is hydrogen, halogen, hydroxyl (—OH), cyano (—CN), 1–4C-alkyl, 1–4C-alkoxy, benzyloxy, nitro (—NO₂), trifluoromethyl (—CF₃), 1–4C-alkoxycarbonyl (—CO—O-1–4C-alkyl), carbamoyl (—CO—NH₂), di-1–4C-alkylcarbamoyl [—CON—(1–4C-alkyl)₂], amino (—NH₂), 1–4C-alkylsulfonyl, phenyl or phenylcarbonylamino and R5 is hydrogen, halogen, hydroxyl (—OH), 1–4C-alkyl or 1–4C-alkoxy, and in which R4 is not hydroxyl or 1–4C-alkoxy if E is oxycarbonyl (—O—CO—), n is the number 0 and Y is a bond, and in which R1 and R2 are not simultaneously hydroxyl if X is 1–4C-alkylene and E is carbonyloxy (—CO—O—), or a salt of this compound.

2. A compound of formula I as claimed in claim 1, in which

X is 1–12C-alkylene or cyclohexylene,

E is carbonyloxy (—CO—O—) or oxycarbonyl (—O—CO—), n is an integer from 0 to 8,

Y is a bond, oxygen (O) or the group —CHR—, in which R is 1–4C-alkyl, phenyl or hydroxyl, and in which Y is not oxygen if n is the number 0, Ar₁ is a phenyl radical substituted by R1, R2 and R3, in which R1 is hydrogen, halogen, hydroxyl (—OH), amino (—NH₂), ureido (—NH—CO—NH₂), formylamino (—NH—COH), 1–4C-alkylcarbonylamino (—NH—CO-1–4C-alkyl), di-1–4C-alkyl-carbamoyloxy [—O—CO—N(1–4C-alkyl)₂], toluyloxy (—O—CO—C₆H₄—CH₃), hydroxymethyl (—CH₂OH), 1–4C-alkylcarbonyloxy (—O—CO-1–4C-alkyl), 1–4C-alkyl, 1–4C-alkoxy, 1–4C-alkylsulfonylamino (—NH—SO₂-1–4C-alkyl), 1–4C-alkylsulfonylmethyl (—CH₂—SO₂-1–4C-alkyl) or 1–4C-alkoxy-1–4C-alkyl, R2 is hydrogen, halogen, hydroxyl (—OH), cyano (—CN), trifluoromethyl (—CF₃), toluyloxy (—O—CO—C₆H₄—CH₃), hydroxymethyl (—CH₂OH) or 1–4C-alkylcarbonyloxy (—O—CO-1–4C-alkyl) and R3 is hydrogen or halogen, and Ar₂ is a phenyl radical substituted by R4 and R5, a thienyl radical, a pyridyl radical or a naphthyl radical, in which R4 is hydrogen, halogen, hydroxyl (—OH), cyano (—CN), 1–4C-alkyl, 1–4C-alkoxy, benzyloxy, nitro (—NO₂), trifluoromethyl (—CF₃), 1–4C-alkoxycarbonyl (—CO—O-1–4C-alkyl), carbamoyl (—CO—NH₂), di-1–4C-alkylcarbamoyl [—CO—N(1–4C-alkyl)₂] or amino (—NH₂) and R5 is hydrogen, halogen, hydroxyl (—OH), 1–4C-alkyl or 1–4C-alkoxy, and in which R4 is not hydroxyl or 1–4C-alkoxy if E is oxycarbonyl (—O—CO—), n is the number 0 and Y is a bond, and in which R1 and R2 are not simultaneously hydroxyl if X is 1–4C-alkylene and E is carbonyloxy (—CO—O—), or a salt of this compound.

3. A compound of formula I as claimed in claim 1, in which n is an integer from 1 to 10, or a salt of this compound.

4. A compound of formula I as claimed in claim 1, in which E is carbonyloxy (—CO—O—), or a salt of this compound.

20

5. A compound of formula I as claimed in claim 1, in which E is oxycarbonyl (—O—CO—), or a salt of this compound.

6. A compound of formula I as claimed in claim 1, in which

X is 1–6C-alkylene, 1–2C-alkyleneoxy-1–2C-alkylene or cyclohexylene,

E is carbonyloxy (—CO—O—) or oxycarbonyl (—O—CO—), n is an integer from 1 to 5,

Y is a bond, oxygen (O) or the group —CHR—, in which R is 1–4C-alkyl,

Ar₁ is a phenyl radical substituted by R1, R2 and R3, in which

R1 is hydrogen, hydroxyl or amino (—NH₂),

R2 is hydrogen, halogen, cyano, trifluoromethyl or hydroxymethyl and

R3 is hydrogen or halogen, and

Ar₂ is a phenyl radical substituted by R4 and R5, a thienyl radical, a pyridyl radical, a naphthyl radical, an indolyl radical or an indanyl radical, in which R4 is hydrogen, halogen, hydroxyl (—OH), cyano (—CN), 1–4C-alkyl, 1–4C-alkoxy, benzyloxy, nitro (—NO₂) or trifluoromethyl (—CF₃), and R5 is hydrogen, halogen or 1–4C-alkyl, or a salt of this compound.

7. A compound of formula I as claimed in claim 1, in which

X is 3–4C-alkylene,

E is carbonyloxy (—CO—O—) or oxycarbonyl (—O—CO—), n is the number 1 or 2,

Y is a bond,

Ar₁ is phenyl, 4-amino-3-chloro-5-cyanophenyl, 4-amino-hydroxy-3-hydroxymethylphenyl or 4-amino-3,5-dichlorophenyl, and Ar₂ is a phenyl radical substituted by R4 and R5 or a 1-naphthyl radical, in which R4 is hydrogen, chlorine, fluorine, hydroxyl (—OH), 1–4C-alkyl or 1–4C-alkoxy and R5 is hydrogen, or a salt of this compound.

8. A compound of formula I as claimed in claim 1, in which

X is 1–6C-alkylene,

E is carbonyloxy (—CO—O—) or oxycarbonyl (—O—CO—), n is an integer from 1 to 3,

Y is a bond, oxygen (O) or the group —CHR—, in which R is 1–4C-alkyl,

Ar₁ is phenyl or 4-amino-3,5-dichlorophenyl, and

Ar₂ is a phenyl radical substituted by R4 and R5, a 3-thienyl radical, a 2-pyridyl radical or a 1-naphthyl radical, in which R4 is hydrogen, fluorine, hydroxyl (—OH), 1–4C-alkyl or 1–4C-alkoxy and R5 is hydrogen or 1–4C-alkyl, or a salt of this compound.

9. A compound as claimed in claim 1, selected from the group consisting of 2-(1-naphthyl)ethyl 6-[2-(4-amino-3,5-dichlorophenyl)-2-hydroxyethylamino]hexanoate, {6-[2-(4-amino-3,5-dichlorophenyl)-2-hydroxyethylamino]-1-hexyl}1-naphthylacetate, 2-(4-hydroxyphenyl)ethyl 6-[2-(4-amino-3,5-dichlorophenyl)-2-hydroxyethylamino]hexanoate, {5-[2-(4-amino-2,3-dichlorophenyl)-2-hydroxyethylamino]-1-pentyl}phenylacetate, 2-(3-hydroxyphenyl)ethyl 6-[2-(4-amino-3,5-dichlorophenyl)-2-hydroxyethylamino]hexanoate,
2-(2-hydroxyphenyl)ethyl 6-[2-(4-amino-3,5-dichlorophenyl)-2-hydroxyethylamino]hexanoate,
2-phenylethyl 6-[2-hydroxy-2-(4-hydroxy-3-hydroxymethylphenyl)ethylamino]hexanoate,
{6-[2-hydroxy-2-(4-hydroxy-3-hydroxymethylphenyl)ethylamino]-1-hexyl}1-naphthylacetate,
2-(3-hydroxyphenyl)ethyl 6-[2-hydroxy-2-(4-hydroxy-3-hydroxymethylphenyl)ethylamino]hexanoate,
4-phenylbutyl 6-[2-hydroxy-2-(4-hydroxy-3-hydroxymethylphenyl)ethylamino]hexanoate,
{6-[2-(4-amino-3,5-dichlorophenyl)-2-hydroxyethylamino]-1-hexyl}3-methoxyphenylacetate,
2-(1-naphthyl)ethyl 6-[2-(4-hydroxy-3-hydroxymethylphenyl)-2-hydroxyethylamino]hexanoate,
2-phenylethyl 6-[2-(4-amino-5-chloro-3-cyanophenyl)-2-hydroxyethylamino]hexanoate,
{6-[2-hydroxy-2-(4-hydroxy-3-hydroxymethylphenyl)ethylamino]-1-hexyl}phenylacetate,
{5-[2-hydroxy-2-(4-hydroxy-3-hydroxymethylphenyl)ethylamino]-1-pentyl}(3-hydroxyphenyl)acetate,
{6-[2-(4-amino-3,5-dichlorophenyl)-2-hydroxyethylamino]-1-hexyl}2-methoxyphenylacetate,
{6-[2-(4-amino-3,5-dichlorophenyl)-2-hydroxyethylamino]-1-hexyl}3-methylphenylacetate,
{6-[2-(4-amino-2,3-dichlorophenyl)-2-hydroxyethylamino]-1-hexyl}2-chlorophenylacetate,
{5-[2-(4-amino-3,5-dichlorophenyl)-2-hydroxyethylamino]-1-pentyl}3-(1-naphthyl)propionate,
{5-[2-hydroxy-2-(4-hydroxy-3-hydroxymethylphenyl)ethylamino]-1-pentyl}3-(1-naphthyl)propionate,
{6-[2-(4-amino-3,5-dichlorophenyl)-2-hydroxyethylamino]-1-hexyl}2-fluorophenylacetate,
2-(3-indolyl)ethyl 6-[2-(4-amino-3,5-dichlorophenyl)-2-hydroxyethylamino]hexanoate and
{2-[2-[2-(4-amino-3,5-dichlorophenyl)-2-hydroxyethylamino]ethoxy]ethyl}phenylacetate or a salt thereof.

10. A medicament composition comprising a suitable carrier and an effect amount of a compound of formula I as claimed in claim 1 or a pharmacologically-tolerated salt thereof.

11. In a method of treating a disease of the bronchi by administering an effective amount of active ingredient to a human or other animal afflicted with such disease, the improvement wherein the active ingredient is a compound of claim 1 or a pharmacologically-tolerated salt thereof.

* * * * *